(12) United States Patent
Oota

(10) Patent No.: US 12,222,348 B2
(45) Date of Patent: Feb. 11, 2025

(54) METHOD OF STORING LATEX PARTICLE DISPERSION LIQUID

(71) Applicants: JSR CORPORATION, Minato-ku (JP); JSR LIFE SCIENCES CORPORATION, Minato (JP); JSR Life Sciences, LLC, Sunnyvale, CA (US); JSR MICRO N.V., Leuven (BE)

(72) Inventor: Kazusa Oota, Minato (JP)

(73) Assignees: JSR CORPORATION, Minato-ku (JP); JSR LIFE SCIENCES CORPORATION, Minato-ku (JP); JSR Life Sciences, LLC, Sunnyvale, CA (US); JSR MICRO N.V., Leuven (BE)

( * ) Notice: Subject to any disclaimer, the term of this patent is extended or adjusted under 35 U.S.C. 154(b) by 1480 days.

(21) Appl. No.: 16/473,835

(22) PCT Filed: Dec. 27, 2017

(86) PCT No.: PCT/JP2017/046977
§ 371 (c)(1),
(2) Date: Jun. 26, 2019

(87) PCT Pub. No.: WO2018/124203
PCT Pub. Date: Jul. 5, 2018

(65) Prior Publication Data
US 2020/0150113 A1 May 14, 2020

(30) Foreign Application Priority Data
Dec. 27, 2016 (JP) .................. 2016-252164

(51) Int. Cl.
| | | |
|---|---|---|
| G01N 33/543 | (2006.01) | |
| C08C 1/065 | (2006.01) | |
| C08F 2/22 | (2006.01) | |
| A61K 39/44 | (2006.01) | |
| B01L 3/00 | (2006.01) | |

(52) U.S. Cl.
CPC ....... G01N 33/54313 (2013.01); C08C 1/065 (2013.01); C08F 2/22 (2013.01); *A61K 39/44* (2013.01); *B01L 3/505* (2013.01)

(58) Field of Classification Search
CPC ....... G01N 33/54313; G01N 33/54333; G01N 33/5434; G01N 33/54346; G01N 33/546; G01N 33/544; G01N 33/543; G01N 33/5485; G01N 33/587; G01N 33/545; G01N 1/4077; B01L 3/52; B01L 3/505; B01L 2300/041; B01L 2300/123; C08C 1/065; C08F 2/22; C08F 212/08; C08F 2/00; C08F 2/18; C08F 2/24; C08F 265/06; A61K 39/44; A61K 49/0002; A61K 49/1818; B65D 83/0055; B65D 77/06; B65D 85/72; C08J 3/16; C08J 2339/06; C08J 3/205; C08J 3/07; C08J 2309/04; C08J 2325/06; C08J 3/09; B29B 2009/125; B29B 9/00; B29B 9/12; C09D 133/08; C09D 133/12; C09D 125/06; B82Y 30/00; B82Y 40/00; C01B 13/36; C08L 25/06; C08L 2312/00; C08L 9/08; C08L 9/10; C09J 109/10; C09J 7/385; Y10T 428/2891
USPC ........ 436/523, 518, 531, 533, 534; 428/407, 428/489; 424/491; 422/547, 555
See application file for complete search history.

(56) References Cited

U.S. PATENT DOCUMENTS

| | | | |
|---|---|---|---|
| 4,636,479 A * | 1/1987 | Martin ............. | G01N 33/54393 436/829 |
| 5,854,083 A | 12/1998 | Chu et al. | |
| 7,867,785 B2 * | 1/2011 | Obana ................ | G01N 33/5434 436/528 |
| 2011/0117671 A1 | 5/2011 | Tanaka | |
| 2015/0059288 A1 | 3/2015 | Wu | |

(Continued)

FOREIGN PATENT DOCUMENTS

| | | |
|---|---|---|
| EP | 3 041 748 | 7/2016 |
| JP | 2-173568 A | 7/1990 |
| JP | 3-84461 A | 4/1991 |

(Continued)

OTHER PUBLICATIONS

Thermo Scientific ("SDS—Polymer Microsphere Suspension" Version 1, Dec. 1, 2015) (Year: 2015).*
Webb (Volume and Density Determinations for Particle Technologists Micromeritics Instrument Corp.(2001). Microsoft Word—Volume and Density for web page.doc (micromeritics.com) (Year: 2001).*

(Continued)

*Primary Examiner* — Christopher L Chin
(74) *Attorney, Agent, or Firm* — Oblon, McClelland, Maier & Neustadt, L.L.P.

(57) ABSTRACT

To provide a novel technique with which the generation of aggregates over time in a dispersion liquid can be suppressed and a target substance can be detected with high sensitivity even if latex particles that have been stored are used. A method for storing in a container a latex particle dispersion liquid in which latex particles for an extracorporeal diagnostic agent are dispersed, the latex particles having a volume average particle size of 10 to 1000 nm and including a polymer containing 70 to 100% by mass of monomer units each derived from a monomer having an aryl group relative to the total monomer units, which is characterized in that the particle dispersion liquid is stored in the container by setting a ratio of a volume of a void space obtained by excluding a volume occupied by the particle dispersion liquid from an internal volume of the container to 0 to 25% (v/v) relative to the internal volume of the container.

16 Claims, No Drawings

(56) References Cited

U.S. PATENT DOCUMENTS

2015/0369826 A1    12/2015    Tetsumoto et al.

FOREIGN PATENT DOCUMENTS

| JP | 8-226921 A | | 9/1996 | |
| JP | 08226921 | * | 9/1996 | |
| JP | H08226921 A | * | 9/1996 | ............. G01N 35/02 |
| JP | 10-509805 A | | 9/1998 | |
| JP | 11-258241 A | | 9/1999 | |
| JP | 2000-81436 A | | 3/2000 | |
| JP | 2000-321279 A | | 11/2000 | |
| JP | 2005-351643 A | | 12/2005 | |
| JP | 2010-19794 A | | 1/2010 | |
| JP | 2011-27552 A | | 2/2011 | |
| JP | 2016-125948 A | | 7/2016 | |
| WO | WO 97/06438 A1 | | 2/1997 | |
| WO | WO 2014/132833 A1 | | 9/2014 | |
| WO | WO 2015/031901 A2 | | 3/2015 | |
| WO | WO 2015/031901 A3 | | 3/2015 | |

OTHER PUBLICATIONS

Kim et al (Emulsifier-Free Emulsion Copolymerization of Styrene and Sodium Styrene Sulfonate Journal of Polymer Science: Part A Polymer Chemistry 30 (1992):171-183. (Year: 1992).*

Gokmen et al("Porous polymer particles—A comprehensive guide to synthesis, characterization, functionalization and applications" Progress in Polymer Science 37 (2012): 365-405) (Year: 2012).*

International Search Report issued on Apr. 3, 2018 in PCT/JP2017/046977 filed on Dec. 27, 2017.

Extended European Search Report issued on Jun. 23, 2020 in corresponding European Patent Application No. 17886852.7, 9 pages.

Duke: "General Purpose Latex Particles; 5000 Series Latex Microsphere Suspensions; 7000 Series Copolymer Microsphere Suspensions; Sales Bulletin 112A; Particle size determined by: Photon Correlation Spectroscopy Optical Microscopy Laser Diffraction", www.jysco.com, Oct. 15, 2005, 4 pages, retrieved from the internet: URL:www.jysco.com/product/download/it/file=20388 [retrieved on Jun. 12, 2020].

* cited by examiner

METHOD OF STORING LATEX PARTICLE DISPERSION LIQUID

TECHNICAL FIELD

The present invention relates to a method for storing a latex particle dispersion liquid, a packaged dispersion liquid, and a kit including the packaged dispersion liquid.

BACKGROUND ART

An immunoagglutination method utilizing antigen-antibody reaction has been widely used in various fields of, for example, clinical examination, and biochemical studies. Especially, the immunoagglutination method using a support, which is typified by a latex agglutination method, is excellent in, for example, detection sensitivity as compared with that of a method for detecting an agglutination reaction without using a support, and therefore, has become the mainstream of the immunoagglutination method.

CITATION LIST

Patent Literature

Patent Literature 1: JP 2000-81436 A

SUMMARY OF INVENTION

Problem to be Solved

The above-described latex agglutination method is generally performed by sensitizing latex particles in a latex particle dispersion liquid in which the latex particles are dispersed in a dispersion medium, and by using the sensitized latex particles.

However, there is a case where latex particles in a latex particle dispersion liquid may agglutinate due to, for example, the processing after production, or the change in storage environment (Patent Literature 1). It is difficult to disperse again the aggregates once generated, and when such aggregates are generated, for example, a false positive attributable to the aggregates is detected even if the latex particle dispersion liquid is used as a diagnostic agent, and therefore, the latex particle dispersion liquid cannot be used as a diagnostic agent.

Further, in the diagnosis by the latex agglutination method, the positive or the negative is determined by the agglutination of latex, and therefore, the latex particles are designed so as to easily agglutinate even by binding to a minute amount of a target substance (for example, an antigen). Therefore, when the dispersibility is increased by, for example, changing the design of the latex particles, the sensitivity may be lowered.

Accordingly, an object to be solved by the present invention is to provide a novel technique with which the generation of aggregates over time in a dispersion liquid can be suppressed and the target substance can be detected with high sensitivity even if latex particles that have been stored are used.

Means for Solving the Problem

As a result of intensive studies on the generation of aggregates over time in a latex particle dispersion liquid, the present inventors found that there is a certain relationship between the ratio of a volume of avoid space obtained by excluding a volume occupied by a latex particle dispersion liquid from an internal volume of a container, and the generation of aggregates over time in the latex particle dispersion liquid.

In addition, as a result of further intensive studies, the present inventors found that by storing a latex particle dispersion liquid in a container so that the ratio of a volume of a void space obtained by excluding a volume occupied by the latex particle dispersion liquid from an internal volume of the container falls within a specific ratio of 0 to 25% (v/v), the generation of aggregates over time in a dispersion liquid can be suppressed and the target substance can be detected with high sensitivity even if latex particles that have been stored are used. Based on these finds, they have completed the present invention.

That is, the present invention provides the following <1> to <11>.

<1> A method for storing in a container a latex particle dispersion liquid in which latex particles for an extracorporeal diagnostic agent are dispersed, the latex particles having a volume average particle size of 10 to 1000 nm and including a polymer containing 70 to 100% by mass of monomer units each derived from a monomer having an aryl group relative to the total monomer units; including setting a ratio of a volume of a void space obtained by excluding a volume occupied by the particle dispersion liquid from an internal volume of the container to 0 to 25% (v/v) relative to the internal volume of the container, to store the latex particle dispersion liquid in the container (hereinafter, also referred to as "storage method of the present invention").

<2> The method for storing in a container described in <1>, in which the latex particle dispersion liquid is stored at a temperature in a range of 1 to 45° C.

<3> The method for storing in a container described in <1> or <2>, in which the particle dispersion liquid has a pH of 3 to 12 at 25° C.

<4> The method for storing in a container described in any one of <1> to <3>, in which the ratio of a volume of the void space is 0 to 7.5% (v/v) relative to the internal volume of the container.

<5> The method for storing in a container described in any one of <1> to <4>, in which the particle dispersion liquid further includes an anionic surfactant.

<6> The method for storing in a container described in any one of <1> to <5>, in which the latex particles have a surface charge amount of 0.15 mmol/g or more.

<7> The method for storing in a container described in any one of <1> to <6>, in which the container is provided with a housing that houses the particle dispersion liquid and is rich in flexibility of being deformed so as to deflate with a decreasing amount of the particle dispersion liquid.

<8> The method for storing in a container described in any one of <1> to <7>, in which the container has a function of keeping the ratio of a volume of the void space constant.

<9> A packaged dispersion liquid, including housing in a container a latex particle dispersion liquid in which latex particles for an extracorporeal diagnostic agent are dispersed, the latex particles having a volume average particle size of 10 to 1000 nm and including a polymer containing 70 to 100% by mass of monomer units each derived from a monomer having an aryl group relative to the total monomer units, in which a ratio of a volume of a void space obtained by excluding a volume occupied by the particle dispersion liquid from an internal volume of the container is set to 0 to 25% (v/v) relative to the internal volume of the container (hereinafter, also referred to as "packaged dispersion liquid of the present invention").

<10> The packaged dispersion liquid described in <9>, in which a CV value of an equivalent circle diameter (number basis) is 50% or less when particles contained in the particle dispersion liquid are measured in a particle size range of 0.8 to 100 μm.

<11> A kit for use in detection of a target substance in a specimen by a latex agglutination method, including the packaged dispersion liquid described in <9> or <10> (hereinafter, also referred to as "kit of the present invention").

Effect of the Invention

According to the storage method and packaged dispersion liquid of the present invention, it is possible to suppress the generation of aggregates over time in a dispersion liquid, and a target substance can be detected with high sensitivity even if latex particles that have been stored are used.

DETAILED DESCRIPTION OF THE INVENTION

[Storage Method]

The storage method of the present invention is a method for storing in a container a latex particle dispersion liquid in which latex particles for an extracorporeal diagnostic agent are dispersed, the latex particles having a volume average particle size of 10 to 1000 nm and including a polymer containing 70 to 100% by mass of monomer units each derived from a monomer having an aryl group relative to the total monomer units, and is characterized in that the particle dispersion liquid is stored in the container by setting the ratio of a volume of a void space obtained by excluding a volume occupied by the particle dispersion liquid from an internal volume of the container (hereinafter, also referred to as "void ratio") to 0 to 25% (v/v) relative to the internal volume of the container.

(Void Ratio)

In the storage method of the present invention, a particle dispersion liquid is stored in a container by setting the void ratio to 0 to 25% (v/v) relative to 100% of the internal volume of the container. When the void ratio is more than 25% (v/v), the generation of aggregates over time are increased, and the sensitivity tends to be easily lowered in a case where a target substance is detected by using latex particles that have been stored.

From the point of enhancing the desired effect of the present invention, the above-described void ratio is preferably 0 to 20% (v/v), more preferably 0 to 15% (v/v), furthermore preferably 0 to 12.5% (v/v), still more preferably 0 to 10% (v/v), still furthermore preferably 0 to 7.5% (v/v), and particularly preferably 0 to 5% (v/v). In particular, by setting the void ratio to be 7.5% (v/v) or less or 5% (v/v) or less, the desired effect of the present invention can be remarkably enhanced, and aggregates are hardly generated even in a case of the long-term storage under high temperature condition.

In this regard, in the storage method of the present invention, both cases of storing by setting the void ratio to 0 to 25% (v/v) in an unopened container and of storing by setting the void ratio to 0 to 25% (v/v) in a container after opening are included.

In the storage method of the present invention, the storage temperature is preferably in a range of 1 to 45° C., more preferably in a range of 2 to 40° C., furthermore preferably in a range of 2 to 30° C., and particularly preferably in a range of 3 to 27° C. According to the storage method of the present invention, even when the storage temperature exceeds the ordinary temperature (for example, 30° C. or more), the generation of aggregates can be suppressed.

(Latex Particles for Extracorporeal Diagnosis)

The latex particles contained in the particle dispersion liquid to be used in the present invention include a polymer containing monomer units each derived from a monomer having an aryl group (hereinafter, also referred to as "monomer (a)"). the latex particles may also be synthetic polymer-based polymer particles or natural polymer-based polymer particles.

As the monomer (a), a monomer having a phenyl group, and a monomer having a naphthyl group can be mentioned, and these monomers may be used singly alone, or in combination of two or more kinds thereof. As the monomer having a phenyl group, a styrene-based monomer is preferred. Specific examples of the monomer having a phenyl group include styrene, α-methyl styrene, aminostyrene, 2-methyl styrene, 4-methyl styrene, 4-chlorostyrene, 4-vinylbenzoic acid, divinylbenzene, and vinyl toluene. Further, as the monomer having a phenyl group, an unsaturated monomer having a naphthyl group is preferred. Specific examples of the monomer having a phenyl group include 1-vinylnaphthalene, 2-vinylnaphthalene, 1-naphthyl (meth)acrylate, and 2-naphthyl (meth)acrylate. Among them, as the monomer (a), a styrene-based monomer is preferred, and styrene is particularly preferred.

The content of the monomer units each derived from a monomer (a) is 70 to 100% by mass relative to the total monomer units. When the content is less than 70% by mass, the detection sensitivity is significantly lowered. From the viewpoint of enhancing the desired effect of the present invention, the content of the monomer units each derived from a monomer (a) is preferably 75 to 99.8% by mass, more preferably 80 to 99.5% by mass, furthermore preferably 85 to 97% by mass, and particularly preferably 90 to 95% by mass, relative to the total monomer units.

Note that the content of each of the monomer units in a polymer can be measured, for example, by nuclear magnetic resonance (NMR).

Further, the above-described polymer may contain monomer units each derived from a monomer other than the monomer (a) (hereinafter, also referred to as "monomer (b)").

Examples of the monomer (b) include an unsaturated carboxylic acid monomer, an unsaturated carboxylic acid anhydride monomer or a salt thereof such as (meth)acrylic acid, itaconic acid, maleic anhydride, crotonic acid, or a salt thereof; an unsaturated sulfonic acid monomer or a salt thereof such as 2-acrylamide-2-methylpropanesulfonic acid, isoprenesulfonic acid, styrenesulfonic acid, divinyl benzenesulfonic acid, 2-methylstyrenesulfonic acid, 4-methylstyrenesulfonic acid, or a salt thereof;

a (meth)acrylamide monomer such as (meth)acrylamide, N-hydroxyethyl (meth)acrylamide, N,N-dimethyl (meth)acrylamide, N-isopropyl (meth)acrylamide, (meth)acryloyl morpholine, N,N-dimethylaminopropyl acrylamide, a methyl chloride quaternary salt of N,N-dimethylaminopropyl acrylamide, diacetone acrylamide, or N-vinylacetamide;

a (meth)acrylate monomer such as methoxyethyl (meth)acrylate, methyl (meth)acrylate, ethyl (meth)acrylate, propyl (meth)acrylate, lauryl (meth)acrylate, cyclohexyl (meth)acrylate, isobornyl (meth)acrylate, benzyl (meth)acrylate, glycerol (meth)acrylate, polyethylene glycol (meth)acrylate, or 2-hydroxyethyl (meth)acrylate;

an unsaturated aldehyde monomer such as acrolein, and further allylamine, and N-vinyl-2-pyrrolidone. These monomers may be used singly alone, or in combination of two or more kinds thereof.

Among them, as the monomer (b), an unsaturated carboxylic acid monomer, an unsaturated carboxylic acid anhydride monomer, an unsaturated sulfonic acid monomer, or a salt thereof is preferred. In this regard, as the salt of an unsaturated carboxylic acid monomer, the salt of an unsaturated carboxylic acid anhydride monomer, and the salt of an unsaturated sulfonic acid monomer, they are not particularly limited, and for example, an alkali metal salt such as a sodium salt, a potassium salt, and a lithium salt; an alkaline earth metal salt such as a calcium salt; and an ammonium salt can be mentioned.

From the viewpoint of enhancing the desired effect of the present invention, the content of monomer units each derived from a monomer (b) is preferably 0 to 30% by mass, more preferably 0.2 to 25% by mass, furthermore preferably 0.5 to 20% by mass, still more preferably 3 to 15% by mass, and particularly preferably 5 to 10% by mass, relative to the total monomer units.

Further, the content of the above-described polymer is preferably 50 to 100% by mass, more preferably 70 to 100% by mass, and particularly preferably 90 to 100% by mass, relative to the total mass of the latex particles for an extracorporeal diagnostic agent.

The latex particles for an extracorporeal diagnostic agent containing the above-described polymer can be produced according to a conventional method. Specifically, a polymerization method using a heat radical generator can be mentioned.

Examples of the heat radical generator include a water-soluble polymerization initiator such as potassium persulfate, sodium persulfate, ammonium persulfate, and 2,2'-azobis(2-methylpropionamidine) dihydrochloride; and an oil-soluble polymerization initiator such as 2,2'-azobis(isobutyronitrile), and bis(3,5,5-trimethylhexanoyl) peroxide. Among them, from the viewpoint of enhancing the desired effect of the present invention, a water-soluble polymerization initiator is preferred, and a persulfate such as potassium persulfate is more preferred. From the viewpoint of enhancing the desired effect of the present invention, the amount of the heat radical generator to be used is preferably 0.01 to 10 parts by mass, more preferably 0.1 to 5 parts by mass, and particularly preferably 0.5 to 2 parts by mass, relative to 100 parts by mass in total of the monomers.

The latex particles contained in the particle dispersion liquid to be used in the present invention have a volume average particle size of 10 to 1000 nm. From the point of the desired effect of the present invention or the production cost, the volume average particle size is preferably 20 to 750 nm, and more preferably 50 to 500 nm.

In the present specification, the volume average particle size means a volume average particle size measured by a dynamic light scattering method, and can be measured by using a particle size distribution analyzer such as Nanotrac particle size distribution analyzer UPA-EX150 (manufactured by NIKKISO CO., LTD.), ALV 5000 (manufactured by ALV-Laser Vertriebsgesellschaft m.b.H.), FPAR-1000 (manufactured by Otsuka Electronics Co., Ltd.), or Zetasizer range (manufactured by Malvern Panalytical Ltd.). In addition, the volume average particle size can be measured also by a method in which a particle dispersion liquid is centrifuged, aggregates are precipitated, and then the supernatant is measured by the above-described particle size distribution analyzer.

From the viewpoint of enhancing the desired effect of the present invention, the surface charge amount of the latex particles contained in the particle dispersion liquid to be used in the present invention is preferably 0 to 20 mmol/g, more preferably 0.01 to 10 mmol/g, furthermore preferably 0.15 to 5 mmol/g, and particularly preferably 0.2 to 2.5 mmol/g. In particular, when the surface charge amount is set to 0.15 mmol/g or more or 0.2 mmol/g or more, the desired effect of the present invention can be remarkably enhanced, and aggregates are hardly generated even in a case of the long-term storage under high temperature condition.

In the present specification, the surface charge amount is a value calculated by determining the amount of titrated sulfuric acid by using a tangent line of the obtained electric conductivity curve when measured by a potentiometric titrator. The measurement can be performed by using a potentiometric titrator such as Titrino series (manufactured by Metrohm AG), TITRA-AI6 (manufactured by HIRANU-MASANGYO Co., Ltd.), or AT-710M (manufactured by Kyoto Electronics Manufacturing Co., Ltd.).

The latex particles may be any latex particles on which a substance capable of binding to a target substance has been supported, or any latex particles on which a substance capable of binding to a target substance has not been supported. That is, in the present invention, the latex particles includes all of the following latex particles: unsupported latex particles on which a substance capable of binding to a target substance can be supported by physical adsorption, latex particles on which a substance capable of binding to a target substance has been supported by physical adsorption, unsupported latex particles on which a substance capable of binding to a target substance can be supported by chemical bonding, and latex particles on which a substance capable of binding to a target substance has been supported by chemical bonding. Among them, from the viewpoint of enhancing the desired effect of the present invention, unsupported latex particles are preferred. In this regard, unsupported latex particles on which a substance capable of binding to a target substance can be supported by physical adsorption, and latex particles on which a substance capable of binding to a target substance has been supported by physical adsorption generally tend to generate aggregates in a dispersion liquid, however, according to the storage method of the present invention, the generation of aggregates over time can be suppressed even in a case where such latex particles are used.

As the substance capable of binding to a target substance, an antigen or antibody against the target substance is preferred. Examples of the substance include an antigen such as a receptor, an enzyme, a protein in blood, an infectious disease-related antigen, a microorganism, a virus, a hormone, and an environment-related substance (for example, environmental hormone), and an antibody against the antigen. The antibody is only required to have binding ability to a specific antigen, and includes a fragment of an antibody.

Specific examples of the antibody include an antibody for a coagulation fibrinolysis-related test, such as an anti-antiplasmin antibody, an anti-D dimer antibody, an anti-FDP antibody, an anti-tPA antibody, an anti-thrombin and anti-thrombin complex antibody, and an anti-FPA antibody, or an antigen against the antibody; an antibody for a tumor-related test, such as an anti-BFP antibody, an anti-CEA antibody, an anti-AFP antibody, an anti-TSH antibody, an anti-ferritin antibody, and an anti-CA19-9 antibody, or an antigen against the antibody; an antibody for a serum protein-related test, such as an anti-apolipoprotein antibody, an anti-β2-microglobulin antibody, an anti-α1-microglobulin antibody, an anti-immunoglobulin antibody, and an anti-CRP antibody, or an antigen against the antibody; an antibody for an endocrine function test, such as an anti-HCG antibody, or an antigen against the antibody; an antibody for drug analysis, such as an anti-digoxin antibody, and an anti-lidocaine antibody, or an antigen against the antibody; an antigen for an infectious disease-related test, such as an HBs antigen, an HCV antigen, an HIV-1 antigen, an HIV-2 antigen, an HTLV-1 antigen, a mycoplasma antigen, a toxoplasma antigen, and a streptolysin O antigen, or an antibody against the antibody; and an antigen for an autoimmunity-related test, such as a DNA antigen, and heat-denatured human IgG, or an antibody against the antibody. In this regard, the antibody may be a polyclonal antibody or a monoclonal antibody.

Further, the supporting of a substance capable of binding to a target substance to a support particle (unsupported particle) may be performed according to a conventional method such as a physical adsorption method by hydrophobic-hydrophobic interaction, or a chemical bonding method using, for example, a water-soluble carbodiimide-based condensing agent.

In addition, the latex particles may be coated with a blocking agent. The blocking agent is not particularly limited as long as it can block non-specific reaction, and examples of the blocking agent include a water-soluble polymer derived from a living body such as bovine serum albumin, and a chemically synthesized water-soluble polymer.

In this regard, the coating with a blocking agent may be performed according to a conventional method such as a method in which latex particles are dispersed in a solution containing a blocking agent, and then the obtained dispersion is subjected to centrifugation, the supernatant is removed, and the obtained latex particles are dispersed again in water or a buffer solution.

The content (in terms of solid content) of the latex particles is preferably 0.001% by mass or more, more preferably 0.005% by mass or more, furthermore preferably 0.01% by mass or more, still more preferably 0.05% by mass or more, and particularly preferably 0.1% by mass or more, and is preferably 50% by mass or less, more preferably 40% by mass or less, furthermore preferably 30% by mass or less, still more preferably 20% by mass or less, still furthermore preferably 15% by mass or less, and particularly preferably 10% by mass or less, relative to the total amount of the particle dispersion liquid.

(Dispersion Medium)

As the dispersion medium in a particle dispersion liquid to be used in the present invention, any dispersion medium may be used as long as it can disperse latex particles for an extracorporeal diagnostic agent. For example, an aqueous medium can be mentioned.

As the aqueous medium, an aqueous medium containing water is preferred. The content of the water is preferably 40 to 100% by mass, more preferably 60 to 100% by mass, furthermore preferably 80 to 100% by mass, and particularly preferably 90 to 100% by mass, relative to the total amount of the aqueous medium.

Further, the aqueous medium may also be a buffer solution such as a Good's buffer solution, a Tris buffer solution, a phosphate buffer solution, a glycine buffer solution, and an ammonia buffer solution.

In this regard, the aqueous medium may contain a lower alcohol such as methanol, ethanol, and isopropanol, in addition to the water or the buffer solution.

The content of the dispersion medium is preferably 50 to 99.9% by mass, more preferably 70 to 99.9% by mass, furthermore preferably 80 to 99.9% by mass, and particularly preferably 85 to 99.9% by mass, relative to the total amount of the particle dispersion liquid.

(Surfactant)

In addition, from the point of enhancing the desired effect of the present invention, as the particle dispersion liquid to be used in the present invention, a particle dispersion liquid containing a surfactant in addition to the above-described respective components is preferred. As to the surfactant, one kind may be used alone, or two or more kinds may be used in combination. Examples of the surfactant include an anionic surfactant, and a nonionic surfactant. Among them, from the point of enhancing the desired effect of the present invention, an anionic surfactant is preferred, a sulfate ester-type anionic surfactant such as sodium dodecyl sulfate, and lithium dodecyl sulfate, and a carboxylic acid-type anionic surfactant such as N-lauroylsarcosine sodium are more preferred, a sulfate ester-type anionic surfactant is furthermore preferred, and sodium dodecyl sulfate is particularly preferred. By using such a surfactant, the desired effect of the present invention can be remarkably enhanced, and aggregates are hardly generated even in a case of the long-term storage under high temperature condition.

From the point of enhancing the desired effect of the present invention, the content of the surfactant is preferably 0 to 10% by mass, and more preferably 0.01 to 1% by mass, relative to the total amount of a particle dispersion liquid.

(pH)

From the point of enhancing the desired effect of the present invention, the pH at 25° C. of the particle dispersion liquid to be used in the present invention is preferably in a range of 3 to 12, more preferably in a range of 5 to 11, furthermore preferably in a range of 7 to 10, still more preferably in a range of more than 7 and 9 or less, and particularly preferably in a range of 8 to 9.

(Container)

The shape of the container to be used in the present invention is not particularly limited as long as the container can store the particle dispersion liquid to be used in the present invention, and as shape of the container, it includes, for example, a shape, such as bottle, pouch, tube, canister, or cup. Further, each of the containers having such a shape can be produced by a known method, and a commercially available container may be used.

In addition, the material for the container is not particularly limited, and the part where the particle dispersion liquid to be used in the present invention directly comes into contact with is preferably made of a material with little metal elution, such as glass or resin. The container made of such a material can be produced by a known method of, for example, JP 59-035043 A. The above-described resin is not particularly limited, and may be a polymer of a single kind of a monomer or a copolymer of two or more kinds of monomers. As the resin, a polyolefin-based resin is preferred. Specific examples of the polyolefin-based resin include polyethylene (for example, low density polyethylene), polypropylene, a cyclic polyolefin, polytetrafluoroethylene, an ethylene and propylene copolymer, and an ethylene and α-olefin copolymer, and these may be used singly alone, or in combination of two or more kinds thereof.

Further, the above-described part may be made of a single layer of these resins or may be made of multiple layers of these resins.

As the container to be used in the present invention, from the point of the easy adjustment to a desired void ratio, a container (hereinafter, also referred to as "container A") provided with a housing that houses a particle dispersion liquid and is rich in flexibility of being deformed so as to deflate with a decreasing amount of the particle dispersion liquid is preferred, and from the point of the transportability, a container provided with the above-described housing (inner container) and an outer container in which the inner container has been installed is more preferred. Further, a container provided with a lid for opening and closing an opening of a housing is preferred.

Examples of the container A include the following containers (1) and (2), and the container (2) is preferred.

(Container (1))

(1) A container provided with an inner container that houses a particle dispersion liquid and is rich in flexibility of being deformed so as to deflate with a decreasing amount of the particle dispersion liquid, an outer container that surrounds the outer periphery of the inner container, and an outer lid that serves as the lid of an opening of the inner container and also as the lid of an opening of the outer container.

As the container (1), it is preferred that the inner container is housed detachably from the outer container. Further, as the inner container, a flexible liner or bag can be mentioned, and an inner container made of the above-described resin is preferred. In addition, as the container (1), a container in which the inner container is fixed to a predetermined position in the outer container by a holding structure such as a lid or a cover.

Further, the outer container is preferably an outer container having rigidity or semi-rigidity, and more preferably a canister-type outer container. For example, as the outer container, an outer container made of the above-described resin or a metal can be mentioned.

As such a container (1), for example, NOWPAK (registered trademark) manufactured by TOHO SHEET & FRAME CO., LTD. can be mentioned.

(Container (2))

(2) A container having a function of keeping the ratio of a volume of a void space constant.

As such a container, for example, a container configured so as to keep the ratio of a volume of the void space constant by, for example, preventing gas from flowing into the inside of a housing by, for example, an air valve, a check valve can be mentioned. Further, the preferred shape of the container (2) is a shape of bottle, or pouch.

As the container (2), the following container (2-1) is preferred from the point that the desired void ratio is easily adjusted and the transportability is excellent.

(2-1) A container provided with a container body having an inner container that houses a particle dispersion liquid and is rich in flexibility of being deformed so as to deflate with a decreasing amount of the particle dispersion liquid, and an outer container in which the inner container is installed and an intake hole for sucking outside air is formed between the inner container and the outer container.

As the container (2-1), specifically, a discharge container can be mentioned, which is provided with: a container body having an inner container that houses a particle dispersion liquid and is rich in flexibility of being deformed so as to deflate with a decreasing amount of the particle dispersion liquid, and an outer container in which the inner container is installed and an intake hole for sucking outside air is formed between the inner container and the outer container; a discharge cap attached to a mouth of the container body and equipped with a discharge port for discharging a particle dispersion liquid; an outside air introduction hole communicating the outside with the intake hole; and an air valve with which the switching of communication or interruption between the outside air introduction hole and the intake hole is performed.

As such a container (2), a container described, for example, in JP 2010-179961 A, JP 2011-219115 A, JP 2013-147295 A, JP 2015-155333 A, or WO 2009/078196 can be mentioned.

In this regard, the means for housing a latex particle dispersion liquid in a container is not particularly limited, and the housing may be performed by a conventional method depending on, for example, the shape of the container.

Further, according to the storage method of the present invention, the generation of aggregates over time in a dispersion liquid can be suppressed and a target substance can be detected with high sensitivity even if latex particles that have been stored are used.

As the dispersion liquid that has been stored, a mode diameter (most frequent diameter) of an equivalent circle diameter (number basis) when particles contained in the dispersion liquid are measured in a particle size range of 0.8 to 100 μm is preferably 0 to 1.3 μm, more preferably 0 to 1.2 μm, furthermore preferably 0 to 1.0 μm, still more preferably 0 to 0.8 m, and particularly preferably 0 (not detected).

In the present specification, the mode diameter (most frequent diameter) means a mode diameter (most frequent diameter) measured by a flow-type image analysis method, and specifically means a value measured in a similar manner as in Examples by using a particle size and shape analyzer, such as FPIA-3000 (manufactured by SYSMEX CORPORATION).

Further, as the dispersion liquid that has been stored, a CV value (coefficient of variation) of an equivalent circle diameter (number basis) when particles contained in the dispersion liquid are measured in a particle size range of 0.8 to 100 μm is preferably 50% or less, and more preferably 30% or less. In this regard, the lower limit value is, for example, 1%.

In addition, the CV value (coefficient of variation) may be measured in a similar manner as in Examples by using the above-described particle size and shape analyzer.

[Packaged Dispersion Liquid]

The packaged dispersion liquid of the present invention is a packaged dispersion liquid obtained by housing in a container a latex particle dispersion liquid in which latex particles for an extracorporeal diagnostic agent are dispersed, the latex particles having a volume average particle size of 10 to 1000 nm and including a polymer that contains 70 to 100% by mass of monomer units each derived from a monomer having an aryl group relative to the total monomer units, and is characterized in that the ratio of a volume of a void space obtained by excluding a volume occupied by the particle dispersion liquid from an internal volume of the container is 0 to 25% (v/v) relative to the internal volume of the container.

In the packaged dispersion liquid of the present invention, in addition to a latex particle dispersion liquid, a container, and a void ratio, a mode diameter (most frequent diameter) and a CV value (coefficient of variation) of an equivalent circle diameter (number basis) when particles contained in the dispersion liquid are measured in a particle size range of 0.8 to 100 μm are preferably similar to those in the above-described storage method.

[Kit]

The kit according to the present invention is a kit for use in detection of a target substance in a specimen by a latex agglutination method, and is provided with the packaged dispersion liquid of the present invention. In a case of being arranged in the kit, the latex particle dispersion liquid is preferably a dispersion liquid in which latex particles on which a substance capable of binding to a target substance has been supported are dispersed.

The kit of the present invention may be provided with a reagent (also referred to as "first reagent") containing one or more kinds selected from a blocking agent and an immunoagglutination enhancer, in addition to the above-described packaged dispersion liquid (also referred to as "second reagent"). As the blocking agent and the immunoagglutination enhancer, for example, a water-soluble polymer derived from a living body such as bovine serum albumin, or a chemically synthesized water-soluble polymer can be mentioned. Further, the first reagent may contain an aqueous medium similar to the aqueous medium described above.

In addition, the kit according to the present invention may be provided with, for example, a positive control, a negative control, and a serum dilution, in addition to the above-described first reagent and second reagent. As the medium of each of the positive control and the negative control, a serum not containing a target substance, or a saline solution may be used, and further a solvent may be used. As the solvent, the aqueous medium described above can be mentioned.

The kit of the present invention can be used for a detection method of a target substance in a similar manner as in the kit for use in detection of a target substance in a specimen by an ordinary latex agglutination method. Further, the concentration of a target substance can also be measured according to a conventional method. The kit of the present invention is useful as a kit for a latex immunoagglutination turbidimetric method.

EXAMPLES

Hereinafter, the present invention will be described in detail with reference to Examples, however, the present invention is not limited to the following Examples.

Preparation Example 1A (Preparation of Latex Particle Dispersion Liquid)

Into a 2-liter glass flask with a stirrer, 25 parts by mass of styrene, 400 parts by mass of water, 0.06 part by mass of sodium dodecylbenzenesulfonate, 0.035 part by mass of sodium hydrogen carbonate, and 0.7 part by mass of potassium persulfate were charged, and the polymerization reaction was performed at 80° C. for 2 hours in the 2-liter glass flask under a nitrogen atmosphere. Next, into the resultant mixture, 0.2 part by mass of sodium dodecylbenzenesulfonate was added, and 75 parts by mass of styrene was added dropwise over 2 hours, and then the polymerization reaction was further performed at 80° C. for 4 hours to obtain particles having a volume average particle size of 355 nm (hereinafter, referred to as "particle 1"). In this regard, the volume average particle size was measured by a Nanotrac particle size distribution analyzer UPA-EX150 (manufactured by NIKKISO CO., LTD.). (In Preparation Examples, the same applies hereinafter.) The obtained particle 1 was purified by dialysis to prepare an aqueous dispersion of particle 1 (having a pH of 9 at 25° C. and a solid content concentration of 10% by mass).

Preparation Example 2A (Preparation of Latex Particle Dispersion Liquid)

Particles having a volume average particle size of 350 nm (hereinafter, referred to as "particle 2") were obtained in the similar manner as in Preparation Example 1-A except that the use amount of potassium persulfate was changed to 0.5 part by mass. The obtained particle 2 was purified by dialysis to prepare an aqueous dispersion of particle 2 (having a pH of 9 at 25° C. and a solid content concentration of 10% by mass).

Preparation Example 3A (Preparation of Latex Particle Dispersion Liquid)

The particle 2 obtained in Preparation Example 2A was purified by dialysis, and then into the purified particle 2, a 2% by mass aqueous solution of sodium dodecyl sulfate was added to prepare an aqueous dispersion of particle 2 (having a pH of 9 at 25° C., a solid content concentration of 10% by mass, and a sodium dodecyl sulfate concentration of 0.5% by mass).

Preparation Example 4A (Preparation of Latex Particle Dispersion Liquid)

Particles having a volume average particle size of 350 nm (hereinafter, referred to as "particle 3") were obtained in the similar manner as in Preparation Example 1A except that the use amount of potassium persulfate was changed to 0.3 part by mass. The obtained particle 3 was purified by dialysis, and then into the purified particle 3, a 2% by mass aqueous solution of sodium dodecyl sulfate was added to prepare an aqueous dispersion of particle 3 (having a pH of 9 at 25° C., a solid content concentration of 10% by mass, and a sodium dodecyl sulfate concentration of 0.5% by mass).

Preparation Example 5A (Preparation of Latex Particle Dispersion Liquid)

Into a 2-liter glass flask with a stirrer, 25 parts by mass of styrene, 400 parts by mass of water, 0.06 part by mass of sodium dodecylbenzenesulfonate, 0.035 part by mass of sodium hydrogen carbonate, and 0.5 part by mass of potassium persulfate were charged, and the polymerization reaction was performed at 80° C. for 2 hours in the 2-liter glass flask under a nitrogen atmosphere. Next, into the resultant mixture, 0.2 part by mass of sodium dodecylbenzenesulfonate was added, and 68 parts by mass of styrene, and 7 parts by mass of methacrylic acid were added dropwise over 2 hours, and then the polymerization reaction was further performed at 80° C. for 4 hours to obtain particles having a volume average particle size of 355 nm and a surface charge amount of 0.2 mmol/g (hereinafter, referred to as "particle 4"). In this regard, the surface charge amount was measured by a potentiometric titrator (794 Basic Titrino manufactured by Metrohm AG). (In Preparation Examples, the same applies hereinafter.) The obtained particle 4 was purified by dialysis to prepare an aqueous dispersion of particle 4 (having a pH of 9 at 25° C. and a solid content concentration of 10% by mass).

Preparation Example 6A (Preparation of Latex Particle Dispersion Liquid)

Particles having a volume average particle size of 350 nm and a surface charge amount of 0.1 mmol/g (hereinafter, referred to as "particle 5") were obtained in the similar manner as in Preparation Example 5A except that the use amount of methacrylic acid was changed to 3.5 parts by mass. The obtained particle 5 was purified by dialysis to prepare an aqueous dispersion of particle 5 (having a pH of 9 at 25° C. and a solid content concentration of 10% by mass).

Preparation Example 7A (Preparation of Latex Particle Dispersion Liquid)

Particles having a volume average particle size of 350 nm and a surface charge amount of 0.05 mmol/g (hereinafter, referred to as "particle 6") were obtained in the similar manner as in Preparation Example 5A except that the use amount of methacrylic acid was changed to 1.8 parts by mass. The obtained particle 6 was purified by dialysis to prepare an aqueous dispersion of particle 6 (having a pH of 9 at 25° C. and a solid content concentration of 10% by mass).

Preparation Example 8A (Preparation of Latex Particle Dispersion Liquid)

The particle 5 obtained in Preparation Example 6A was purified by dialysis, and then an aqueous dispersion of particle 5 having a pH of 5 at 25° C. and a solid content concentration of 10% by mass was prepared with the pH adjustment by hydrochloric acid.

Preparation Example 9A (Preparation of Latex Particle Dispersion Liquid)

The particle 5 obtained in Preparation Example 6A was purified by dialysis, and then an aqueous dispersion of particle 5 having a pH of 3 at 25° C. and a solid content concentration of 10% by mass was prepared with the pH adjustment by hydrochloric acid.

Examples 1 to 8 and Comparative Examples 1 to 4 (Storage of Latex Particle Dispersion Liquid)

Each of the latex particle dispersion liquids obtained in Preparation Examples 1A to 9A was housed in a container so that a void ratio was the value shown in the following Table 1, and was stored under the storage conditions shown in Table 1, respectively. In this regard, the void ratio was calculated from a volume of the housed latex particle dispersion liquid and an internal volume of the container.

TABLE 1

| | | Particles | | | Particle dispersion liquid | | Container | | |
|---|---|---|---|---|---|---|---|---|---|
| | Species | St (% by mass) | MA (% by mass) | Surface charge amount (mmol/g) | Preparation Example | SDS addition | Type | Void ratio (% (v/v)) | Storage conditions |
| Example 1 | Particle 1 | 100 | 0 | — | 1A | Not added | PE bottle | 5 | 25° C. for 1 week |
| Example 2 | Particle 6 | 98 | 2 | 0.05 | 7A | Not added | PE bottle | 10 | 25° C. for 1 week |
| Example 3 | Particle 2 | 100 | 0 | — | 2A | Not added | PE bottle | 20 | 25° C. for 1 week |
| Example 4 | Particle 5 | 96 | 4 | 0.1 | 6A | Not added | PE bottle | 20 | 25° C. for 1 week |
| Comparative Example 1 | Particle 3 | 100 | 0 | — | 4A | Added | PE bottle | 30 | 25° C. for 1 week |
| Comparative Example 2 | Particle 5 | 96 | 4 | 0.1 | 8A | Not added | PE bottle | 40 | 25° C. for 1 week |
| Comparative Example 3 | Particle 5 | 96 | 4 | 0.1 | 9A | Not added | PE bottle | 40 | 25° C. for 1 week |
| Example 5 | Particle 3 | 100 | 0 | — | 4A | Added | Bottle K | 0 | 37° C. for 1 month |
| Example 6 | Particle 3 | 100 | 0 | — | 4A | Added | Pouch Y | 0 | 37° C. for 1 month |
| Example 7 | Particle 4 | 93 | 7 | 0.2 | 5A | Not added | PE bottle | 10 | 37° C. for 1 month |
| Example 8 | Particle 2 | 100 | 0 | — | 3A | Added | PE bottle | 20 | 37° C. for 1 month |
| Comparative Example 4 | Particle 2 | 100 | 0 | — | 2A | Not added | PE bottle | 40 | 37° C. for 1 month |

Each of the symbols in Table 1 is as follows.
St: Content of monomer units derived from styrene
MA: Content of monomer units derived from methacrylic acid
SDS: Sodium dodecyl sulfate
PE bottle: Polyethylene bottle (square type, internal capacity of 500 mL)
Bottle K: Bottle of "Freshly squeezed raw soy sauce at any time" manufactured by Kikkoman Corporation, from which the soy sauce inside was withdrawn, the bottle was washed thoroughly and then filled with a particle dispersion liquid.
Pouch Y: Pouch of "Drop of Freshness" manufactured by YAMASA CORPORATION, from which the soy sauce inside was withdrawn, the pouch was washed thoroughly and then filled with a particle dispersion liquid.

Test Example 1: Microscopic Observation

After completion of the storage of each of Examples and Comparative Examples, a particle dispersion liquid was sufficiently stirred by shaking the container, and then 10 μL of the particle dispersion liquid was applied dropwise on a slide glass, and the particle dispersion liquid on the slide glass was observed with an optical microscope (at 400-fold magnification, CS SERIES manufactured by Carton Optical Industries, Ltd.), and evaluated according to the following criteria. The results are shown in Table 2.

(Evaluation Criteria)
- AA: No aggregates were confirmed
- A: Only a few aggregates were confirmed
- B: Aggregates were clearly confirmed
- C: Many large aggregates were confirmed Test Example 2: Particle Size Measurement After completion of the storage of each of Examples and Comparative Examples, a particle dispersion liquid was sufficiently stirred by shaking the container, and then 500 μL of the particle dispersion liquid was weighed out, and with respect to the particles contained in this dispersion liquid, the mode diameter (most frequent diameter) of an equivalent circle diameter (number basis) in a particle size range of 0.8 to 100 μm was measured by a flow-type image analysis method using a particle size and shape analyzer FPIA-3000 (manufactured by SYSMEX CORPORATION). The results are shown in Table 2. It can be said that as the value of the mode diameter is smaller, the generation of aggregates (secondary particles) over time of primary particles is more suppressed.

Test Example 3: CV Value Measurement

With respect to the particle dispersion liquid stored in each of Example 8 and Comparative Example 3, the CV value of an equivalent circle diameter (number basis) was measured when the particle dispersion liquid was evaluated with FPIA-3000 (manufactured by SYSMEX CORPORATION) in Test Example 2. The results are shown in Table 2. It can be said that as the CV value is smaller, the generation of aggregates (secondary particles) over time of primary particles is more suppressed.

TABLE 2

|  | Evaluation by microscopic observation | Mode diameter [μm] | CV value [%] |
|---|---|---|---|
| Example 1 | AA | 0 (not detected) | — |
| Example 2 | A | 1.2 | — |
| Example 3 | A | 1.1 | — |
| Example 4 | A | 1.1 | — |
| Comparative Example 1 | C | 1.9 | — |
| Comparative Example 2 | B | 1.4 | — |
| Comparative Example 3 | C | 1.7 | 72 |
| Example 5 | AA | 0 (not detected) | — |
| Example 6 | AA | 0 (not detected) | — |
| Example 7 | AA | 0 (not detected) | — |
| Example 8 | AA | 0 (not detected) | 21 |
| Comparative Example 4 | C | 1.8 | — |

From the results of Table 2, it was revealed that in a case where a dispersion liquid was stored in a container so that the void ratio was 0 to 25% (v/v) (Examples 1 to 8), the generation of aggregates over time in the dispersion liquid was suppressed.

Preparation Example 1-1B (Preparation of Sensitized Latex Particle Dispersion Liquid)

The latex particles that had been stored by the storage method of Example 1 were sensitized with an anti-human CRP antibody, and a sensitized latex particle dispersion liquid was prepared. The specific procedures are as follows.

The particle dispersion liquid (having a solid content concentration of 10% by mass) that had been stored by the storage method of Example 1 was diluted 10 times with a 50 mM Tris buffer solution (pH 7.4). On the other hand, the aqueous solution of anti-human CRP antibody (10 mg/mL) was diluted twice with a 50 mM Tris buffer solution (pH 7.4).

Next, 6 parts by volume of a diluent of the particle dispersion liquid and 1 part by volume of a diluent of the anti-human CRP antibody were mixed, and the obtained mixture was stirred at 37° C. for 1 hour, and then the mixture was subjected to centrifugation to remove the supernatant. Next, into the mixture obtained above, 7.5 parts by volume of a 50 mM Tris buffer solution (pH 7.4) containing 2% (w/v) bovine serum albumin (BSA) was added, and the obtained mixture was stirred at 25° C. for 1 hour. Further, into the resultant mixture, a 50 mM Tris buffer solution (pH 7.4) containing 1% (w/v) BSA was added to dilute the mixture, as a result of which a sensitized latex particle dispersion liquid (having a solid content concentration of 0.1% by mass) was prepared.

Preparation Example 1-2B (Preparation of Sensitized Latex Particle Dispersion Liquid)

The latex particles that had been stored by the storage method of Example 2 were sensitized with an anti-human CRP antibody, and a sensitized latex particle dispersion liquid was prepared. The specific procedures are as follows.

The particle dispersion liquid (having a solid content concentration of 10% by mass) that had been stored by the storage method of Example 2 was diluted 10 times with a 50 mM Tris buffer solution (pH 7.4). On the other hand, the aqueous solution of anti-human CRP antibody (10 mg/mL) was diluted twice with a 50 mM Tris buffer solution (pH 7.4).

Next, 6 parts by volume of a diluent of the particle dispersion liquid and 1 part by volume of a diluent of the anti-human CRP antibody were mixed, and the obtained mixture was stirred at 37° C. for 1 hour. Into the mixture obtained above, 0.025 part by volume of a 1% by mass aqueous solution of 1-ethyl-3-(3-dimethylaminopropyl)carbodiimide hydrochloride was added, and the mixture was further stirred at 37° C. for 1 hour, and then the resultant mixture was subjected to centrifugation to remove the supernatant. Next, into the mixture obtained above, 7.5 parts by volume of a 50 mM Tris buffer solution (pH 7.4) containing 2% (w/v) BSA was added, and the obtained mixture was stirred at 25° C. for 1 hour. Further, into the resultant mixture, a 50 mM Tris buffer solution (pH 7.4) containing 1% (w/v) BSA was added to dilute the mixture, as a result of which a sensitized latex particle dispersion liquid (having a solid content concentration of 0.1% by mass) was prepared.

Preparation Example 1-33 (Preparation of Sensitized Latex Particle Dispersion Liquid)

The latex particles that had been stored by the storage method of Example 3 were sensitized with an anti-human CRP antibody, and a sensitized latex particle dispersion liquid was prepared.

That is, a sensitized latex particle dispersion liquid (having a solid content concentration of 0.1% by mass) was prepared in the similar manner as in Preparation Example 1-1B except that the particle dispersion liquid that had been stored by the storage method of Example 1 was changed to the particle dispersion liquid that had been stored by the storage method of Example 3.

Preparation Example 1-4B (Preparation of Sensitized Latex Particle Dispersion Liquid)

The latex particles that had been stored by the storage method of Example 4 were sensitized with an anti-human CRP antibody, and a sensitized latex particle dispersion liquid was prepared.

That is, a sensitized latex particle dispersion liquid (having a solid content concentration of 0.1% by mass) was prepared in the similar manner as in Preparation Example 1-2B except that the particle dispersion liquid that had been stored by the storage method of Example 2 was changed to the particle dispersion liquid that had been stored by the storage method of Example 4 and the use amount of a 1% by mass aqueous solution of 1-ethyl-3-(3-dimethylaminopropyl)carbodiimide hydrochloride was changed to 0.05 part by volume.

Preparation Example 1-5B and Preparation Example 1-6B (Preparation of Sensitized Latex Particle Dispersion Liquid)

The latex particles that had been stored by the storage method of each of Examples 5 and 6 were sensitized with an anti-human CRP antibody, and a sensitized latex particle dispersion liquid was prepared.

That is, a sensitized latex particle dispersion liquid (having a solid content concentration of 0.1% by mass) was prepared in the similar manner as in Preparation Example 1-1B except that the particle dispersion liquid that had been stored by the storage method of Example 1 was changed to the particle dispersion liquid that had been stored by the storage method of Example 5 or the particle dispersion liquid that had been stored by the storage method of Example 6.

Preparation Example 1-7B (Preparation of Sensitized Latex Particle Dispersion Liquid)

The latex particles that had been stored by the storage method of Example 7 were sensitized with an anti-human CRP antibody, and a sensitized latex particle dispersion liquid was prepared.

That is, a sensitized latex particle dispersion liquid (having a solid content concentration of 0.1% by mass) was prepared in the similar manner as in Preparation Example 1-2B except that the particle dispersion liquid that had been stored by the storage method of Example 2 was changed to the particle dispersion liquid that had been stored by the storage method of Example 7 and the use amount of a 1% by mass aqueous solution of 1-ethyl-3-(3-dimethylaminopropyl)carbodiimide hydrochloride was changed to 0.1 part by volume.

Preparation Example 1-8B (Preparation of Sensitized Latex Particle Dispersion Liquid)

The latex particles that had been stored by the storage method of Example 8 were sensitized with an anti-human CRP antibody, and a sensitized latex particle dispersion liquid was prepared.

That is, a sensitized latex particle dispersion liquid (having a solid content concentration of 0.1% by mass) was prepared in the similar manner as in Preparation Example 1-1B except that the particle dispersion liquid that had been stored by the storage method of Example 1 was changed to the particle dispersion liquid that had been stored by the storage method of Example 8.

Preparation Example 2-1B (Preparation of Sensitized Latex Particle Dispersion Liquid)

The latex particles that had been stored by the storage method of Comparative Example 1 were sensitized with an anti-human CRP antibody, and a sensitized latex particle dispersion liquid was prepared.

That is, a sensitized latex particle dispersion liquid (having a solid content concentration of 0.1% by mass) was prepared in the similar manner as in Preparation Example 1-1B except that the particle dispersion liquid that had been stored by the storage method of Example 1 was changed to the particle dispersion liquid that had been stored by the storage method of Comparative Example 1.

Preparation Example 2-2B and Preparation Example 2-3B (Preparation of Sensitized Latex Particle Dispersion Liquid)

The latex particles that had been stored by the storage method of each of Comparative Examples 2 and 3 were sensitized with an anti-human CRP antibody, and a sensitized latex particle dispersion liquid was prepared.

That is, a sensitized latex particle dispersion liquid (having a solid content concentration of 0.1% by mass) was prepared in the similar manner as in Preparation Example 1-2B except that the particle dispersion liquid that had been stored by the storage method of Example 2 was changed to the particle dispersion liquid that had been stored by the storage method of Comparative Example 2 or the particle dispersion liquid that had been stored by the storage method of Comparative Example 3 and the use amount of a 1% by mass aqueous solution of 1-ethyl-3-(3-dimethylaminopropyl)carbodiimide hydrochloride was changed to 0.05 part by volume.

Preparation Example 2-4B (Preparation of Sensitized Latex Particle Dispersion Liquid)

The latex particles that had been stored by the storage method of Comparative Example 4 were sensitized with an anti-human CRP antibody, and a sensitized latex particle dispersion liquid was prepared.

That is, a sensitized latex particle dispersion liquid (having a solid content concentration of 0.1% by mass) was prepared in the similar manner as in Preparation Example 1-1B except that the particle dispersion liquid that had been stored by the storage method of Example 1 was changed to the particle dispersion liquid that had been stored by the storage method of Comparative Example 4.

Test Example 3: Latex Immunoagglutination Measurement

By using each of the sensitized latex particle dispersion liquids prepared above, latex immunoagglutination measurement was performed under the following measurement conditions.

That is, 3 μL of a specimen and 100 μL of a specimen diluent were added into a measurement cell, and into the measurement cell, 100 μL of a specimen diluent was added, and the resultant mixture was stirred, and then held for 5 minutes. After that, into the mixture obtained above, 100 μL of the sensitized latex particle dispersion liquid shown in Table 3 was added, and the obtained mixture was stirred. The difference between the absorbance after the lapse of 8 seconds from the start of stirring and the absorbance after the lapse of 300 seconds from the start of stirring (hereinafter, referred to as "Δ absorbance") was measured. The results are shown in Table 3.

<Measurement Conditions>

Measurement device: Hitachi 7180-type Automatic Analyzer
Measurement wavelength: 570 nm
Measurement temperature: 37° C.
Specimen: standard solution at 60 mg/dL
Specimen diluent: 50 mM Tris buffer solution (pH 7.4) containing 1% (w/v) BSA

TABLE 3

|  | Sensitized latex particle dispersion liquid | Δ Absorbance |
| --- | --- | --- |
| Example 1 | 1-1B | 2500 |
| Example 2 | 1-2B | 1400 |
| Example 3 | 1-3B | 1100 |
| Example 4 | 1-4B | 1200 |
| Comparative Example 1 | 2-1B | 300 |
| Comparative Example 2 | 2-2B | 800 |
| Comparative Example 3 | 2-3B | 600 |
| Example 5 | 1-5B | 2600 |
| Example 6 | 1-6B | 2700 |
| Example 7 | 1-7B | 2500 |
| Example 8 | 1-8B | 2200 |
| Comparative Example 4 | 2-4B | 600 |

From the results of Table 3, it was revealed that in a case where a dispersion liquid was stored in a container so that the void ratio was 0 to 25% (v/v) (Examples 1 to 8), the target substance was able to be detected with high sensitivity even by using the latex particles that have been stored.

Further, each of the sensitized latex particle dispersion liquids was prepared in a similar manner as in the above except that the latex particles were not stored before sensitization, and each of the sensitized latex particle dispersion liquids was stored in a similar manner as in Examples 1 to 8 and Comparative Examples 1 to 4 after sensitization, and then when the absorbance measurement was performed, the tendency similar to that in the results of Table 3 was shown.

The invention claimed is:

1. A method for storing in a container a latex particle dispersion liquid in which latex particles for an extracorporeal diagnostic agent are dispersed, the latex particles having a volume average particle size of 10 to 1000 nm and comprising a polymer comprising 70 to 100% by mass of monomer units each derived from a monomer having an aryl group relative to the total monomer units, the method comprising setting a ratio of a volume of a void space obtained by excluding a volume occupied by the latex particle dispersion liquid from an internal volume of the container to 0 to 25% (v/v) relative to the internal volume of the container, and putting the latex particle dispersion liquid in the container in an amount to satisfy the ratio and to store the latex particle dispersion liquid in the container, wherein the container is provided with a housing that houses the latex particle dispersion liquid and that has a flexibility of being deformed so as to deflate with a decreasing amount of the latex particle dispersion liquid.

2. The method of claim 1, wherein the latex particle dispersion liquid is stored at a temperature in a range of 1 to 45° C.

3. The method of claim 1, wherein the latex particle dispersion liquid has a pH of 3 to 12 at 25° C.

4. The method of claim 1, wherein a ratio of a volume of the void space is 0 to 7.5% (v/v) relative to the internal volume of the container.

5. The method of claim 1, wherein the latex particle dispersion liquid further comprises an anionic surfactant.

6. The method of claim 1, wherein the latex particles have a surface charge amount of 0.15 mmol/g or more.

7. The method of claim 1, wherein the container has a function of keeping a ratio of a volume of the void space constant.

8. The method of claim 1, wherein the ratio is 0 to 20% (v/v).

9. The method of claim 1, wherein the ratio is 0 to 10% (v/v).

10. The method of claim 1, wherein the ratio is 0 to 7.5% (v/v).

11. The method of claim 1, wherein the ratio is 0 to 5% (v/v).

12. The method of claim 1, wherein the container comprises an inner container housed detachably from an outer container and the latex particle dispersion liquid is put into the inner container in an amount to satisfy the ratio.

13. A packaged dispersion liquid, comprising a container comprising a latex particle dispersion liquid in which latex particles for an extracorporeal diagnostic agent are dispersed, the latex particles having a volume average particle size of 10 to 1000 nm and comprising a polymer comprising 70 to 100% by mass of monomer units each derived from a monomer having an aryl group relative to the total monomer units, wherein a ratio of a volume of a void space obtained by excluding a volume occupied by the latex particle dispersion liquid from an internal volume of the container is 0 to 25% (v/v) relative to the internal volume of the container, wherein the container is provided with a housing that houses the latex particle dispersion liquid and that has a flexibility of being deformed so as to deflate with a decreasing amount of the latex particle dispersion liquid.

14. The packaged dispersion liquid of claim 13, wherein a CV value of an equivalent circle diameter (number basis) is 50% or less when particles comprised in the latex particle dispersion liquid are measured in a particle size range of 0.8 to 100 μm.

15. A kit for use in detection of a target substance in a specimen by a latex agglutination method, comprising the packaged dispersion liquid of claim 13.

16. The packaged dispersion liquid of claim 13, wherein the container is provided with a housing that houses the latex particle dispersion liquid and that has a flexibility of being deformed so as to deflate with a decreasing amount of the latex particle dispersion liquid.

* * * * *